United States Patent

Smidt et al.

[11] Patent Number: 5,885,787
[45] Date of Patent: Mar. 23, 1999

[54] PROCESS FOR PREPARING OPTICALLY ACTIVE AMINES

[75] Inventors: Hauke Smidt, Wageningen, Netherlands; Andreas Fischer, Freiburg, Germany; Peter Fischer; Rolf D. Schmid, both of Stuttgart, Germany; Uwe Stelzer, Burscheid, Germany

[73] Assignee: Bayer Aktiengesellschaft, Leverkusen, Germany

[21] Appl. No.: 894,668

[22] PCT Filed: Mar. 1, 1996

[86] PCT No.: PCT/EP96/00835

§ 371 Date: Aug. 25, 1997

§ 102(e) Date: Aug. 25, 1997

[87] PCT Pub. No.: WO96/27022

PCT Pub. Date: Sep. 6, 1996

[30] Foreign Application Priority Data

Mar. 2, 1995 [DE] Germany .............. 195 07 217.0

[51] Int. Cl.$^6$ .......................... C10Q 1/34; C07C 209/00; C07C 211/00; C07B 57/00
[52] U.S. Cl. ........................ 435/8; 564/302; 564/303; 564/304; 564/463; 435/27; 435/22
[58] Field of Search .................... 564/302, 303, 564/304, 463; 435/18, 27, 22

[56] References Cited

FOREIGN PATENT DOCUMENTS 399589  11/1990  European Pat. Off. .

OTHER PUBLICATIONS

Rossi, J. Org. Chem., vol. 44, No. 13, 1979, "Approach to the Use of Benzylpenicillinacylase for configurational Coorelations of Amino Compounds . . . " 2222–2225.

Ogawa, Bioorganic & Medicinal Chemistry, vol. 2, No. 2, pp. 429–432, 1994, Enzymatic Asymmetric Synthesis of α–Methyl Arylalkylalcohols by Arylalkyl Acylamidases.

Margolin, A.L., Synthesis of Optically Pure Mechanism–Based Inhibitors of γ–Aminobutyric Acid Aminotransferase (GABA–T) via Enzyme–Catalyzed Resolution, Tetrahedron Lett., 34, 1239–42, 1993.

*Primary Examiner*—Jose' G. Dees
*Assistant Examiner*—Alton Pryor
*Attorney, Agent, or Firm*—Sprung Kramer Schaefer & Briscoe

[57] ABSTRACT

In accordance with a novel process, (R)-amines of the formula

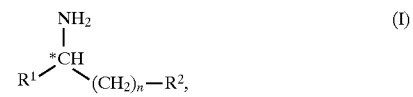

in which $R^1$, $R^2$ and n have the meanings given in the description, can be prepared by reacting reating N-acyl-amines of the formula

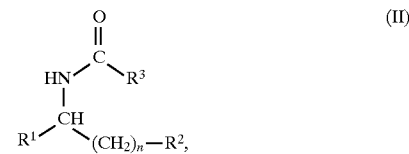

in which $R^1$, $R^2$, $R^3$ and n have the meanings given in the description, with lipases which are suitable for cleaving the (R)-enantiomers of N-acyl-amines of the formula (II), in the presence of water and optionally in the presence of an organic diluent, at a pH of between 3.0 and 10.0 and at temperatures of between 0° C. and 80° C.

5 Claims, No Drawings

PROCESS FOR PREPARING OPTICALLY ACTIVE AMINES

The present invention relates to a novel process for preparing (R)-amines by the enzymic hydrolysis of N-acylamine racemates.

It has already become known to prepare optically active N-p-aminophenyl-acetylamino derivatives by the enzymic cleavage of the corresponding racemates using benzylpenicillin acylase as biocatalyst (cf. J. Org. Chem. 44 2222 2225 (1979). However, a disadvantage of this process is that the optical yields are very low in some cases. In addition, the (S)-enantiomer of the starting racemate is preferentially hydrolysed in this method. Thus, for example, the (R)-enantiomer of N-p-amino-1-phenylacetyl-1-phenethylamine and the free (S)-amine are formed from the corresponding racemate. A further disadvantage is that the biocatalyst reacts in a very substrate-specific manner and only those compounds which contain a phenylacetyl group can be employed.

It is furthermore known that (S)-amines and (R)-enantiomers can be prepared from N-acylated 1-methyl-1-phenyl-alkylamines by means of converting racemates of N-acyl-1-methyl-1-phenyl-alkylamines using particular biocatalysts (cf. EP-A 0 399 589). This process suffers from the disadvantage that the corresponding (R)-amines can only be obtained if the (R)-enantiomers of the N-acyl-1-methyl-1-phenyl-alkylamines are deacylated in an additional reaction step.

It has now been found that (R)-amines of the formula

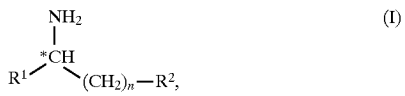

in which $R^1$ represents optionally substituted alkyl, $R^2$ represents optionally substituted alkyl, optionally substituted cycloalkyl, optionally substituted cycloalkenyl, optionally substituted aryl or optionally substituted heterocyclyl, where, however, $R^1$ and $R^2$ are not identical, and n represents the numbers 0, 1, 2 or 3, are obtained by reacting racemic N-acylamines of the formula

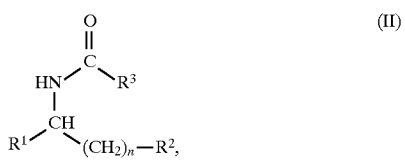

in which $R^1$, $R^2$ and n have the abovementioned meanings, and $R^3$ represents hydrogen, amino, dialkylamino, alkylthio, optionally substituted alkyl or optionally substituted alkoxy, where the carbon chain in those radicals which contain more than one carbon atom can be interrupted by heteroatoms or heteroatom groups, or $R^3$ represents optionally substituted cycloalkyl, optionally substituted cycloalkenyl, optionally substituted aryl or optionally substituted heterocyclyl, with lipases which are suitable for cleaving the (R)-enantiomers of N-acyl-amines of the formula (II), in the presence of water and optionally in the presence of an organic diluent, at a pH of between 3.0 and 10.0 and at temperatures of between 0° C. and 80° C.

(R)-Amines are understood to mean those optically active compounds of the formula (I) which exhibit the (R) configuration at the asymmetrically substituted carbon atom. In the formula (I), the asymmetrically substituted carbon atom is indicated by (*)

It is extremely surprising that (R)-amines can be prepared by the process according to the invention, since the state of the art has hitherto only disclosed that (S)-amines can be obtained from racemates of N-acylamines using biocatalysts.

The process according to the invention enjoys a number of advantages. Thus, it enables (R)-amines of the formula (I) to be prepared in extremely high optical purity. It is also advantageous that the N-acylamines which are required as starting compounds are readily accessible and that the acyl radical can be varied over a wide range. Finally, no difficulties are involved, either, in implementing the reaction and isolating the desired substances.

In the present case, unless otherwise defined, alkyl represents saturated aliphatic hydrocarbon radicals which can be straight-chain or branched.

In the present case, unless otherwise defined, cycloalkyl represents saturated carbocyclic radicals which optionally form a bicyclic or polycyclic ring system with other fused or bridged rings.

In the present case, unless otherwise defined, cycloalkenyl represents unsaturated carbocyclic radicals which optionally form a bicyclic or polycylic ring system with other fused or bridged rings.

In the present case, unless otherwise defined, aryl represents aromatic, monocyclic, bicyclic or polycyclic hydrocarbon radicals such as, for example, phenyl, naphthyl, anthranyl or phenanthryl, preferably phenyl or naphthyl, in particular phenyl.

In the present case, unless otherwise defined, heterocyclyl represents saturated or unsaturated cyclic radicals in which at least one ring member is a heteroatom, i.e. an atom which is different from carbon. If the ring contains several heteroatoms, these can then be identical or different. Preferred heteroatoms are oxygen, nitrogen or sulphur. Where appropriate, the cyclic radicals form a bicyclic or polycyclic ring system jointly with other carbocyclic or heterocyclic, fused or bridged rings. Monocyclic or bicyclic ring systems are preferred, in particular monocyclic or bicyclic ring systems having an aromatic character.

In the present case, unless otherwise defined, halogen represents fluorine, chlorine, bromine or iodine, preferably fluorine, chlorine or bromine, in particular fluorine or chlorine.

If racemic N-[1-(4-chlorophenyl)-ethyl]-acetamide is used as the starting compound and lipase from *Candida antarctica* is used as the biocatalyst, the course of the process according to the invention can then be illustrated by the following formula scheme.

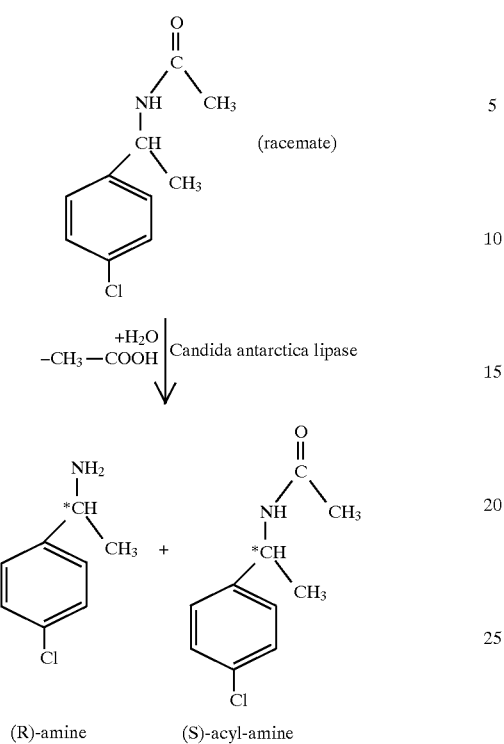

(racemate)

(R)-amine    (S)-acyl-amine

The racemic N-acylamines which are required as starting compounds when carrying out the novel process are generally defined by the formula (II).

$R^1$ preferably represents straight-chain or branched alkyl having from 1 to 8 carbon atoms, where the alkyl radicals can be substituted identically or differently, once or more than once, by halogen, cyano, amino, hydroxyl, formyl, carboxyl, carbamoyl, in each case straight-chain or branched alkoxy or alkylthio having in each case from 1 to 6 carbon atoms;

in each case straight-chain or branched halogenoalkoxy or halogenoalkylthio having in each case from 1 to 6 carbon atoms and from 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case from 1 to 6 carbon atoms in the individual alkyl moieties;

or by doubly linked alkylene having from 1 to 6 carbon atoms or by doubly linked dioxyalkylene having from 1 to 4 carbon atoms, where the two latter radicals can themselves be substituted identically or differently, once or more than once, by halogen, straight-chain or branched alkyl having from 1 to 4 carbon atoms and/or straight-chain or branched halogenoalkyl having from 1 to 4 carbon atoms and from 1 to 9 identical or different halogen atoms.

$R^2$ preferably represents cycloalkyl having from 3 to 7 carbon atoms, where these radicals can be substituted identically or differently, once to four times, by halogen and/or alkyl having from 1 to 4 carbon atoms, or represents cycloalkenyl having from 3 to 7 carbon atoms, where these radicals can be substituted identically or differently, once to four times, by halogen and/or alkyl having from 1 to 4 carbon atoms, or represents saturated or unsaturated, optionally benzofused, heterocyclyl having from 3 to 7 ring members in the heterocycle, of which in each case from 1 to 3 are identical or different heteroatoms, such as oxygen, nitrogen or sulphur, where the radicals can be substituted identically or differently, once to three times, by halogen, alkyl having from 1 to 4 carbon atoms, alkoxy having from 1 to 4 carbon atoms and/or halogenoalkyl having from 1 to 4 carbon atoms and from 1 to 5 identical or different halogen atoms, or $R^2$ preferably represents aryl having from 6 to 10 carbon atoms, where each of these radicals can be substituted identically or differently, once to five times, by halogen, cyano, nitro, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case from 1 to 6 carbon atoms;

in each case straight-chain or branched alkenyl or alkenyloxy having in each case from 2 to 6 carbon atoms;

in each case straight-chain or branched halogenoalkyl, halogenoalkoxy, halogenoalkylthio, halogenoalkylsulphinyl or halogenoalkylsulphonyl having in each case from 1 to 6 carbon atoms and from 1 to 13 identical or different halogen atoms;

in each case straight-chain or branched halogenoalkenyl or halogenoalkenyloxy having in each case from 2 to 6 carbon atoms and from 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case from 1 to 6 carbon atoms in the individual alkyl moieties;

phenyl, phenoxy, phenylthio, benzyloxy, benzylthio or phenylethyloxy, or by doubly linked alkylene having 3 or 4 carbon atoms or by doubly linked dioxyalkylene having 1 or 2 carbon atoms, where the two latter radicals can themselves be substituted identically or differently, once or more than once, by halogen, straight-chain or branched alkyl having from 1 to 4 carbon atoms and/or straight-chain or branched, halogenoalkyl having from 1 to 4 carbon atoms and from 1 to 9 identical or different halogen atoms.

n also preferably represents the numbers 0, 1, 2 or 3.

$R^3$ preferably represents hydrogen, amino, dialkylamino having from 1 to 6 carbon atoms in each alkyl moiety, alkylthio having from 1 to 6 carbon atoms, straight-chain or branched alkyl having from 1 to 10 carbon atoms or straight-chain or branched alkoxy having from 1 to 6 carbon atoms, where the alkyl radicals or alkoxy radicals can be substituted identically or differently, once or more than once, by halogen, cyano, nitro, amino, hydroxyl, formyl, carboxyl, carbamoyl;

in each case straight-chain or branched alkoxy, alkylthio, alkylsulphinyl or alkylsulphonyl having in each case from 1 to 6 carbon atoms;

in each case straight-chain or branched alkenyl or alkenyloxy having in each case from 2 to 6 carbon atoms;

in each case straight-chain or branched halogenoalkoxy, halogenoalkylthio, halogenoalkylsulphinyl or halogenoalkylsulphonyl having in each case from 1 to 6 carbon atoms and from 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case from 1 to 6 carbon atoms in the individual alkyl moieties;

or by doubly linked alkylene having from 1 to 6 carbon atoms or by doubly linked dioxyalkylene having from 1 to 4 carbon atoms, where the two latter radicals can themselves be substituted identically or differently, once or more than once, by halogen, straight-chain or branched alkyl having from 1 to 4 carbon atoms and/or straight-chain or branched halogenoalkyl having from 1 to 4 carbon atoms and from 1 to 9 identical or different halogen atoms, or by phenyl, or $R^3$ preferably represents cycloalkyl having from 3 to 7 carbon atoms, where these radicals can be substituted identically or differently, once to four times, by halogen and/or alkyl having from 1 to 4 carbon atoms, or represents cycloalkenyl having from 3 to 7 carbon atoms, where these radicals can be substituted identically or differently, once to four times, by halogen and/or alkyl having from 1 to 4 carbon atoms, or $R^3$ preferably represents saturated or unsaturated heterocyclyl having from 3 to 7 ring members, of which in each case from 1 to 3 are identical or different heteroatoms, such as oxygen, nitrogen or sulphur, where the radicals can be substituted identically or differently, once to three times, by halogen, alkyl having from 1 to 4 carbon atoms, alkoxy having from 1 to 4 carbon atoms and/or halogenoalkyl having from 1 to 4 carbon atoms and from 1 to 5 identical or different halogen atoms, or $R^3$ preferably represents aryl having from 6 to 10 carbon atoms, where each of these radicals can be substituted identically or differently, once to five times, by halogen, cyano, straight-chain or branched alkyl having from 1 to 4 carbon atoms, straight-chain or branched halogenoalkyl having from 1 to 4 carbon atoms and from 1 to 9 identical or different halogen atoms, straight-chain or branched alkoxy or alkylthio having from 1 to 4 carbon atoms, straight-chain or branched halogenoalkoxy or halogenoalkylthio having from 1 to 4 carbon atoms and from 1 to 9 identical or different halogen atoms, phenyl, phenoxy, phenylthio, benzyloxy, benzylthio or phenylethyloxy, or by doubly linked alkylene having 3 or 4 carbon atoms or by doubly linked dioxyalkylene having 1 or 2 carbon atoms, where the two latter radicals can themselves be substituted identically or differently, once or more than once, by halogen, straight-chain or branched alkyl having from 1 to 4 carbon atoms and/or straight-chain or branched halogenoalkyl having from 1 to 4 carbon atoms and from 1 to 9 identical or different halogen atoms.

$R^1$ particularly preferably represents methyl, ethyl or n-propyl.

$R^2$ particularly preferably represents cyclohexyl, norbornyl or cyclohexenyl, where these radicals can be substituted identically or differently, once to four times, by fluorine, chlorine, methyl and/or ethyl, or represents furyl, pyridyl, thienyl, benzofuryl, quinolyl or benzothienyl, which can be substituted identically or differently, once to three times, by fluorine, chlorine, bromine, methyl, ethyl, n-propyl, i-propyl, n-butyl, i-butyl, s-butyl, t-butyl, methoxy, ethoxy, n-propoxy, i-propoxy, trifluoromethyl and/or trifluoroethyl, or $R^2$ particularly preferably represents phenyl or naphthyl, where each of these radicals can be substituted identically or differently, once to five times, by fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, methoxycarbonyl, ethoxycarbonyl, phenyl, phenoxy, phenylthio, benzyloxy, benzylthio or phenylethyloxy, or by trimethylene (propane-1,3-diyl), methylenedioxy or ethylenedioxy which are in each case doubly linked and which are in each case optionally substituted identically or differently, once or more than once, by fluorine, chlorine, methyl, trifluoromethyl, ethyl or n- or i-propyl.

n also particularly preferably represents the numbers 0, 1, 2 or 3.

$R^3$ particularly preferably represents hydrogen, amino, dimethylamino, methylthio, methyl, ethyl, n- or i-propyl, n-, i- or s-butyl, pentyl, hexyl, heptyl, octyl, methoxy, ethoxy, methoxymethyl, hydroxymethyl, 1-hydroxy-1-ethyl, 2-hydroxycarbonyl-1-hydroxy-1-ethyl, 2-hydroxycarbonyl-1-ethyl, 3-hydroxycarbonyl-1-propyl and benzyl.

The racemic N-acylamines of the formula (II) are either known or can be prepared by acylation of amines in accordance with known methods. Thus, N-acylamines of the formula (II) are obtained, for example, by reacting racemic amines with acid chlorides or acid anhydrides.

When carrying out the process according to the invention, those lipases come into consideration as biocatalysts which are suitable for selectively cleaving the (R)-enantiomers of N-acylamines of the formula (II). Examples which may be mentioned are lipase from *Candida antarctica, Newlase F,* lipase from *Pseudomonas sp. and lipase M*. The lipases which can be employed as biocatalysts are known.

When carrying out the process according to the invention, the lipases can be employed either in the native or in modified form, for example microencapsulated or bound to inorganic or organic support materials. Examples of support materials which are suitable in this context are celite, zeolites, polysaccharides, polyamides and polystyrene resins.

All the solvents which are customary for reactions of this nature come into consideration as organic diluents which can be employed when carrying out the process according to the invention. Those which are preferably utilizable are alcohols, such as methanol, ethanol, n-butanol, benzyl alcohol and phenethyl alcohol, also ethers, such as tetrahydrofuran and dioxane, and, in addition, hydrocarbons, such as pentane and hexane, and, furthermore, amides, such as dimethylformamide, or else strongly polar solvents, such as dimethyl sulphoxide. Finally, emulsifiers and surface-active substances which can function as phase-transfer catalysts also come into consideration as organic diluents. Those which preferably come into consideration are alkylaryl polyglycol ethers, polyethylene oxide fatty acid esters, polyethylene oxide fatty alcohol ethers and ethoxylates of 4-(1, 1,3,3-tetramethylbutyl)-phenol.

All the customary buffering systems come into consideration for adjusting the desired pH when carrying out the process according to the invention. Those which are preferably utilizable are sodium dihydrogen phosphate/disodium hydrogen phosphate mixtures, citrate buffers, glycine buffers and other mixtures of suitable acids and bases.

When carrying out the process according to the invention, the pH can be varied within a defined range. In general, the process is carried out at pH values of between 3.0 and 10.0, preferably between 4.0 and 9.0.

When carrying out the process according to the invention, the reaction temperatures can be varied within a defined range. In general, the process is carried out at temperatures of between 0° C. and 80° C., preferably between 20° C. and 70° C.

When carrying out the process according to the invention, the concentrations of racemic N-acyl-amines of the formula (II) can be varied within a defined range. In general, reaction mixtures are used in which the concentration of racemic N-acylarnine of the formula (II) is between 1 and 200 g/liter, preferably between 2 and 100 g/liter.

When carrying out the process according to the invention, from 0.01 to 200 g, preferably from 0.05 to 100 g, of biocatalyst are generally employed per 1 g of racemic N-acyl-amine of the formula (II). The working-up is effected in accordance with customary methods. In general, the approach is to separate off the biocatalyst and to isolate the desired components from the remaining reaction mixture by means of distillation, fractional crystallization, acid-base solvent extraction or by other means. When this is done, the (R)-amines of the formula (I) either result in the free state or in the form of salts from which the (R)-amines can be liberated by treating with a base. In addition, the (S)-enantiomers of the N-acylamines of the formula (II) can also be separated from the reaction mixture. The latter enantiomers can be converted into the free (S)-amines or their acid addition salts by an additional chemical reaction step, for example acidic or basic hydrolysis, or by enzymic means.

The (R)-amines of the formula (I) which can be prepared by the process according to the invention are valuable intermediates for preparing pharmaceuticals or active compounds possessing insecticidal, fungicidal or herbicidal properties (cf. EP-A 0 519 211, EP-A 0 453 137, EP-A 0 283 879, EP-A 0 264 217 and EP-A 0 341 475). Thus, for example, the fungicidally active compound of the formula

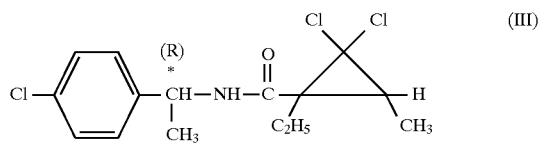

is obtained by reacting the (R)-1-(4-chloro-phenyl)-ethylamine of the formula

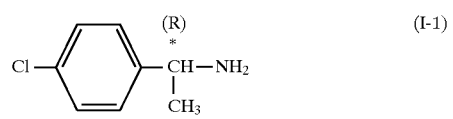

with 2,2-dichloro-1-ethyl-3-methyl-1-cyclopropanecarbonyl chloride of the formula

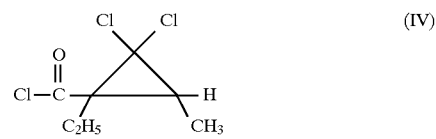

in the presence of an acid-binding agent and in the presence of an inert organic diluent.

The implementation of the process according to the invention is illustrated by the following examples.

PREPARATION EXAMPLES

Example 1

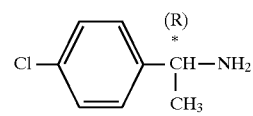

A mixture of 50 mg of racemic N-[1-(4-chloro-phenyl)-ethyl]-acetamide and 100 mg of *Candida antarctica* lipase (Novozym 435®; E.C. no. 3.1.1.3) was made up to a volume of 10 ml using a 50 mM aqueous solution of a sodium dihydrogen phosphate/disodium hydrogen phosphate buffer mixture. The reaction mixture, which had a pH of 8, was shaken at 50° C. for 168 hours. After that, it was centrifuged for 5 minutes and the liquid phase was then analysed. For this purpose, a defined volume was removed from the mixture and frozen at −60° C. for one hour and subsequently freeze-dried. The dry sample was extracted with methanol for one hour while adding a molecular sieve and while treating repeatedly and vigorously with a vortex shaker. The anhydrous, methanolic phase which was obtained after centrifuging was analysed by gas chromatography. A conventional reversed phase RP 18 column was used in the HPLC analysis in order to determine the concentrations of racemic amine and racemic N-acetylamine when ascertaining the conversion.

A mixture of acetonitrile/20 mM phosphate buffer, pH 2.0, 80:20 (v/v) was used as the mobile phase. A wavelength of 220 nm was employed for the UV detection. A calibration by the external standard method was carried out both for the racemic amine and for the N-acetyl-amine. Capillary gas chromatography was employed for the chiral analysis. A capillary glass column having a length of 20 m was used as the column. A chiral mixed phase was used as separating material, while H$_2$ having a carrier gas pressure of 0.4 bar served as the carrier gas. A temperature gradient of 80° C.//1 min iso/2.5° C./min//150° C.//10° C./min//200° C. was employed.

The enantiomeric excess (ee-value), which is calculated as follows:

$$ee = \frac{(R-S)}{(R+S)} \times 100\%$$

was invoked for assessing the enantioselectivity of the reaction.

In this equation, R and S denote the concentrations of the individual enantiomers of the amine which has been formed.

In this way, it is found that the (R)-1-(4-chloro-phenyl)-ethylamine was formed in a yield of 43% and with an ee value of >99%.

Example 2

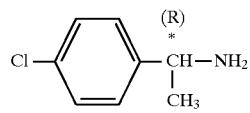

A mixture of 3 mg of racemic N-[1-(4-chloro-phenyl) ethyl]-acetamide and 0.75 mg of purified free lipase B from *Candida antarctica* was made up to a volume of 1.5 ml using a 50 mM aqueous solution of a sodium dihydrogen phosphate/disodium hydrogen phosphate buffer mixture. The reaction mixture, which had a pH of 8, was shaken at 30° C. for 360 hours. After that, it was worked up and analysed in the manner described in Example 1. By these means, it is found that the (R)-1-(4-chlorophenyl)-ethylamine was formed in a yield of 25% and with an ee value of >99%.

Example 3

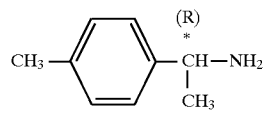

A mixture of 1.3 mg of racemic N-[1-(4-methylphenyl)-ethyl]-acetamide and 15 mg of *Candida antarctica* lipase (Novozym 435®; E.C. No. 3.1.1.3) was made up to a volume of 1.5 ml using a 50 mM aqueous solution of a sodium dihydrogen phosphate/disodium hydrogen phosphate buffer mixture. The reaction mixture, which had a pH of 8, was shaken at 50° C. for 400 hours. After that, it was worked up and analysed in the manner described in Example 1. By these means, it is found that the (R)-1-(4-methylphenyl)-ethylamine was formed in a yield of 32% and with an ee value of >90%.

Example 4

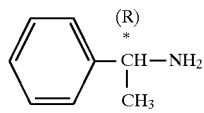

A mixture of 1.2 mg of racemic N-(1-phenyl-ethyl)-acetamide and 15 mg of *Candida antarctica* lipase (Novozym 435®; E.C. No. 3.1.1.3) was made up to a volume of 1.5 ml using a 50 mM aqueous solution of a sodium dihydrogen phosphate/disodium hydrogen phosphate buffer mixture. The reaction mixture, which had a pH of 8, was shaken at 50° C. for 400 hours. After that, it was worked up and analysed in the manner described in Example 1. By these means, it is found that the (R)-1-phenyl-ethylamine was formed in a yield of 7.6% and with an ee value of >90%.

Example 5

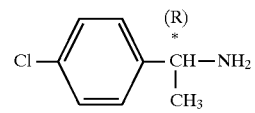

A mixture of 200 mg (0.88 mmol) of racemic N-[1-(4-chloro-phenyl)-ethyl]-methoxy-acetamide and 50 U of *Candida antarctica* lipase (Novozym 435®) was made up to a volume of 7 ml using a 50 mM aqueous solution of sodium dihydrogen phosphate/disodium dihydrogen phosphate buffer mixture. The reaction mixture, which had a pH value of 8, was shaken at 40° C. for 48 hours. The reaction mixture was then extracted three times with di-isopropyl-ether. The combined organic phases were concentrated under reduced pressure. The remaining residue was gas-chromatographically analysed by means of a chiral column. By these means, it was found that the reaction had proceeded with a conversion rate of 48%. The (R)-1-(4-chloro-phenyl)-ethyl-amine formed showed an ee value of 99%.

An ee value of 92% was determined for the (S)-N-[1-(4-chloro-phenyl)-ethyl]-methoxy-acetamide.

We claim:

1. Process for preparing R-amines of the formula

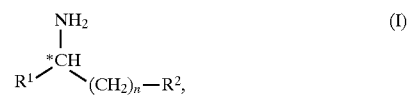

in which

R$^1$ represents optionally substituted alkyl,

R$^2$ represents optionally substituted alkyl, optionally substituted cycloalkyl, optionally substituted cycloalkenyl, optionally substituted aryl or optionally substituted heterocyclyl, where, however, R$^1$ and R$^2$ are not identical, and n represents the numbers 0, 1, 2 or 3, characterized in that racemic N-acylamines of the formula

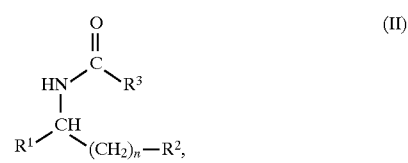

in which

R$^1$, R$^2$ and n have the abovementioned meanings, and

R$^3$ represents hydrogen, amino, dialkylamino, alkylthio, optionally substituted alkyl or optionally substituted alkoxy, where the carbon chain in those radicals which contain more than one carbon atom can be interrupted by heteroatoms or heteroatom groups, or R$^3$ represents optionally substituted cycloalkyl, optionally substituted cycloalkenyl, optionally substituted aryl or optionally substituted heterocyclyl, are reacted with lipases which are suitable for cleaving the (R)-enantiomers of N-acyl-amines of the formula (II), in the presence of water and optionally in the presence of an organic diluent, at a pH of between 3.0 and 10.0 and at temperatures of between 0° C. and 80° C., wherein the lipases which are suitable for cleaving the (R)-enantiomers of N-acyl-amines of the formula (II) are selected from the group consisting of lipases from *Candida antarctica, Newlase F. Pseudomonas sp.* and lipase M.

2. Process according to claim 1, characterized in that racemic N-acylamines of the formula (II) are employed in which $R^{12}$ represents straight-chain or branched alkyl having from 1 to 8 carbon atoms, where the alkyl radicals can be substituted identically or differently, once or more than once, by halogen, cyano, amino, hydroxyl, formyl, carboxyl, carbamoyl, in each case straight-chain or branched alkoxy or alkylthio having in each case from 1 to 6 carbon atoms;

in each case straight-chain or branched halogenoalkoxy or halogenoalkylthio having in each case from 1 to 6 carbon atoms and from 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case from 1 to 6 carbon atoms in the individual alkyl moieties;

or by doubly linked alkylene having from 1 to 6 carbon atoms or by doubly linked dioxyalkylene having from 1 to 4 carbon atoms, where the two latter radicals can themselves be substituted identically or differently, once or more than once, by halogen, straight-chain or branched alkyl having from 1 to 4 carbon atoms and/or straight-chain or branched halogenoalkyl having from 1 to 4 carbon atoms and from 1 to 9 identical or different halogen atoms, $R^2$ represents cycloalkyl having from 3 to 7 carbon atoms, where these radicals can be substituted identically or differently, once to four times, by halogen and/or alkyl having from 1 to 4 carbon atoms, or $R^2$ represents cycloalkenyl having from 3 to 7 carbon atoms, where these radicals can be substituted identically or differently, once to four times, by halogen and/or alkyl having from 1 to 4 carbon atoms, or $R^2$ represents saturated or unsaturated, optionally benzofused heterocyclyl having from 3 to 7 ring members in the heterocycle, of which in each case from 1 to 3 are identical or different heteroatoms, such as oxygen, nitrogen or sulphur, where the radicals can be substituted identically or differently, once to three times, by halogen, alkyl having from 1 to 4 carbon atoms, alkoxy having from 1 to 4 carbon atoms and/or halogenoalkyl having from 1 to 4 carbon atoms and from 1 to 5 identical or different halogen atoms, or $R^2$ represents aryl having from 6 to 10 carbon atoms, where each of these radicals can be substituted identically or differently, once to five times, by halogen, cyano, nitro, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case from 1 to 6 carbon atoms;

in each case straight-chain or branched alkenyl or alkenyloxy having in each case from 2 to 6 carbon atoms;

in each case straight-chain or branched halogenoalkyl, halogenoalkoxy, halogenoalkylthio, halogenoalkylsulphinyl or halogenoalkylsulphonyl having in each case from 1 to 6 carbon atoms and from 1 to 13 identical or different halogen atoms;

in each case straight-chain or branched halogenoalkenyl or halogenoalkenyloxy having in each case from 2 to 6 carbon atoms and from 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case from 1 to 6 carbon atoms in the individual alkyl moieties;

phenyl, phenoxy, phenylthio, benzyloxy, benzylthio or phenylethyloxy, or by doubly linked alkylene having 3 or 4 carbon atoms or by doubly linked dioxyalkylene having 1 or 2 carbon atoms, where the two latter radicals can themselves be substituted identically or differently, once or more than once, by halogen, straight-chain or branched alkyl having from 1 to 4 carbon atoms and/or straight-chain or branched halogenoalkyl having from 1 to 4 carbon atoms and from 1 to 9 identical or different halogen atoms, n represents the numbers 0, 1, 2 or 3 and $R^3$ represents hydrogen, amino, dialkylamino having from 1 to 6 carbon atoms in each alkyl moiety, alkylthio having from 1 to 6 carbon atoms, straight-chain or branched alkyl having from 1 to 10 carbon atoms or straight-chain or branched alkoxy having from 1 to 6 carbon atoms, where the alkyl radicals or alkoxy radicals can be substituted identically or differently, once or more than once, by halogen, cyano, nitro, amino, hydroxyl, formyl, carboxyl, carbamoyl;

in each case straight-chain or branched alkoxy, alkylthio, alkylsulphinyl or alkylsulphonyl having in each case from 1 to 6 carbon atoms;

in each case straight-chain or branched alkenyl or alkenyloxy having in each case from 2 to 6 carbon atoms;

in each case straight-chain or branched halogenoalkoxy, halogenoalkylthio, halogenoalkylsulphinyl or halogenoalkylsulphonyl having in each case from 1 to 6 carbon atoms and from 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case from 1 to 6 carbon atoms in the individual alkyl moieties;

or by doubly linked alkylene having from 1 to 6 carbon atoms or by doubly linked dioxyalkylene having from 1 to 4 carbon atoms, where the two latter radicals can themselves be substituted identically or differently, once or more than once, by halogen, straight-chain or branched alkyl having from 1 to 4 carbon atoms and/or straight-chain or branched halogenoalkyl having from 1 to 4 carbon atoms and from 1 to 9 identical or different halogen atoms, or by phenyl, or $^3$ represents cycloalkyl having from 3 to 7 carbon atoms, where these radicals can be substituted identically or differently, once to four times, by halogen and/or alkyl having from 1 to 4 carbon atoms, or $R^3$ represents cycloalkenyl having from 3 to 7 carbon atoms, where these radicals can be substituted identically or differently, once to four times, by halogen and/or alkyl having from 1 to 4 carbon atoms, or $R^3$ represents saturated or unsaturated heterocyclyl having from 3 to 7 ring members, of which in each case from 1 to 3 are identical or different heteroatoms, such as oxygen, nitrogen or sulphur, where the radicals can be substituted identically or differently, once to three times, by halogen, alkyl having from 1 to 4 carbon atoms, alkoxy having from 1 to 4 carbon atoms and/or halogenoalkyl having from 1 to 4 carbon atoms and from 1 to 5 identical or different halogen atoms, or $R^3$ represents aryl having from 6 to 10 carbon atoms, where each of these radicals can be substituted identically or differently, once to five times, by halogen, cyano, straight-chain or branched alkyl having from 1 to 4 carbon atoms, straight-chain or branched halogenoalkyl having from 1 to 4 carbon atoms and from 1 to 9 identical or different halogen atoms, straight-chain or branched alkoxy or alkylthio having from 1 to 4 carbon atoms, straight-chain or branched halogenoalkoxy or halogenoalkylthio having from 1 to 4 carbon atoms and from 1 to 9 identical or different halogen atoms, phenyl, phenoxy, phenylthio, benzyloxy, benzylthio or phenylethyloxy, or by doubly linked alkylene having 3 or 4 carbon atoms or by doubly linked dioxyalkylene having 1 or 2 carbon atoms, where the two latter radicals can themselves be substituted identically or differently, once or more than once, by halogen, straight-chain or branched alkyl having from 1 to 4 carbon atoms and/or straight-chain or branched halogenoalkyl having from 1 to 4 carbon atoms and from 1 to 9 identical or different halogen atoms.

3. Process according to claim 1, characterized in that the compound of the formula

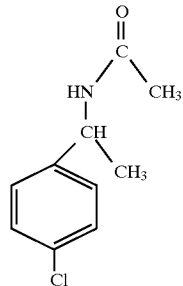

is employed as the racemic N-acylamine.

4. Process according to claim 1, characterized in that it is carried out at a pH of between 4.0 and 9.0.

5. Process according to claim 1, characterized in that it is carried out at temperatures of between 20° C. and 70° C.

* * * * *

UNITED STATES PATENT AND TRADEMARK OFFICE
CERTIFICATE OF CORRECTION

PATENT NO. : 5,885,787
DATED : March 23, 1999
INVENTOR(S) : Smidt et al.

It is certified that error appears in the above-identified patent and that said Letters Patent is hereby corrected as shown below:

Col. 11, Line 6          Delete "$R^{1a}$" and substitute --$R^1$--

Col. 12, Line 58         Delete "$^3$" and substitute --$R^3$--

Signed and Sealed this

Ninth Day of May, 2000

Attest:

Q. TODD DICKINSON

*Attesting Officer*          *Director of Patents and Trademarks*